United States Patent [19]

Kranz

[11] Patent Number: 4,562,598
[45] Date of Patent: Jan. 7, 1986

[54] JOINT PROSTHESIS

[75] Inventor: Curt Kranz, Berlin, Fed. Rep. of Germany

[73] Assignee: Mecron Medizinische Produkte GmbH, Berlin, Fed. Rep. of Germany

[21] Appl. No.: 448,914

[22] PCT Filed: Apr. 1, 1982

[86] PCT No.: PCT/DE82/00078
§ 371 Date: Dec. 1, 1982
§ 102(e) Date: Dec. 1, 1982

[87] PCT Pub. No.: WO82/03323
PCT Pub. Date: Oct. 14, 1982

[51] Int. Cl.⁴ .................... A61F 1/00; A61F 5/04
[52] U.S. Cl. ................................ 623/18; 128/92 C; 128/92 CA; 128/92 BC; 128/92 B; 623/20; 623/22
[58] Field of Search .................. 3/1, 1.9, 1.91, 1.911, 3/1.912, 1.913, 4, 2, 6, 19, 17 R, 36; 128/82, 89 R, 90, 92 R, 92 C, 92 CA

[56] References Cited

U.S. PATENT DOCUMENTS

| | | | |
|---|---|---|---|
| 3,643,656 | 2/1972 | Young et al. | 128/91 A |
| 3,681,787 | 8/1972 | Perras | 3/36 |
| 4,274,163 | 6/1981 | Malcom | 128/92 C |
| 4,357,716 | 11/1982 | Brown | 128/92 CA |
| 4,399,814 | 8/1983 | Pratt, Jr. et al. | 128/92 R |

FOREIGN PATENT DOCUMENTS

| | | | |
|---|---|---|---|
| 0006415 | 1/1980 | European Pat. Off. | 3/1.9 |
| 0016480 | 10/1980 | European Pat. Off. | 3/1.913 |

Primary Examiner—Richard J. Apley
Assistant Examiner—David J. Isabella
Attorney, Agent, or Firm—Spencer & Frank

[57] ABSTRACT

A joint prosthesis for insertion in a bone cavity comprises an adapter; a hollow, flexible prepreg member of hardenable material secured to the adapter; a hollow inflatable pressing member disposed in the prepreg member; and an arrangement for introducing fluid into the pressing member for inflating the same for causing the prepreg member to conform to the walls of the bone cavity.

22 Claims, 5 Drawing Figures

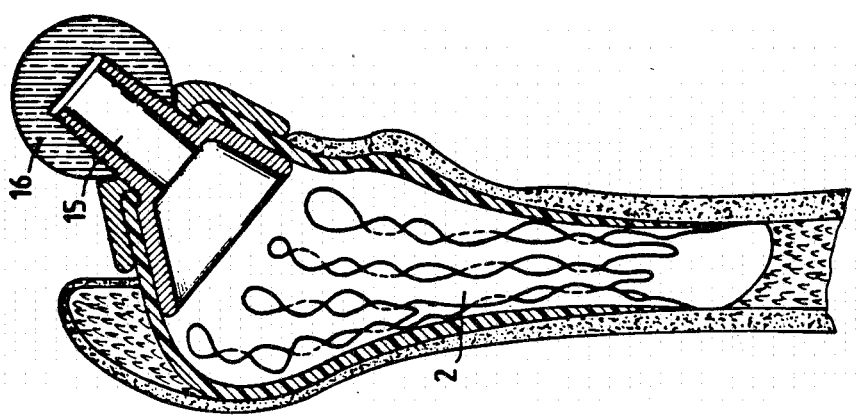
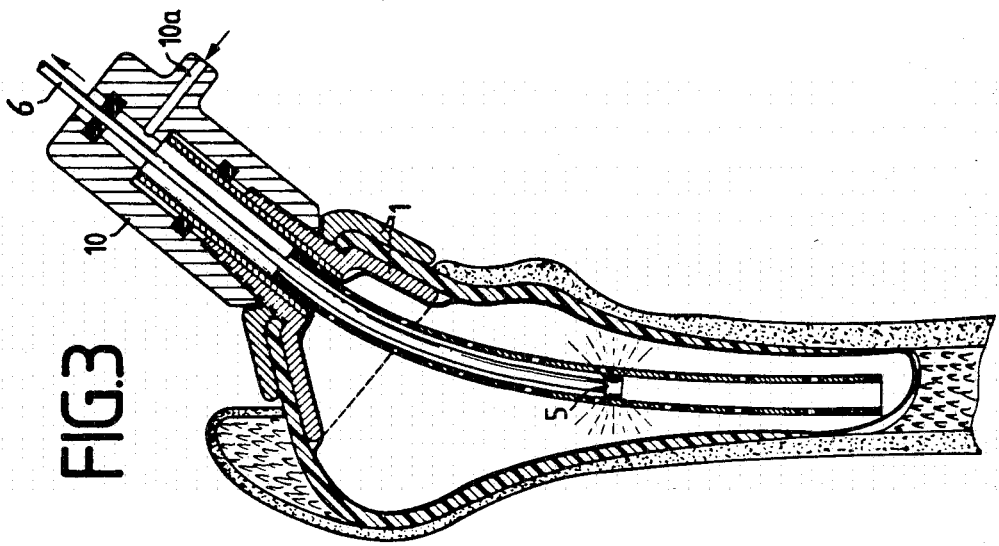
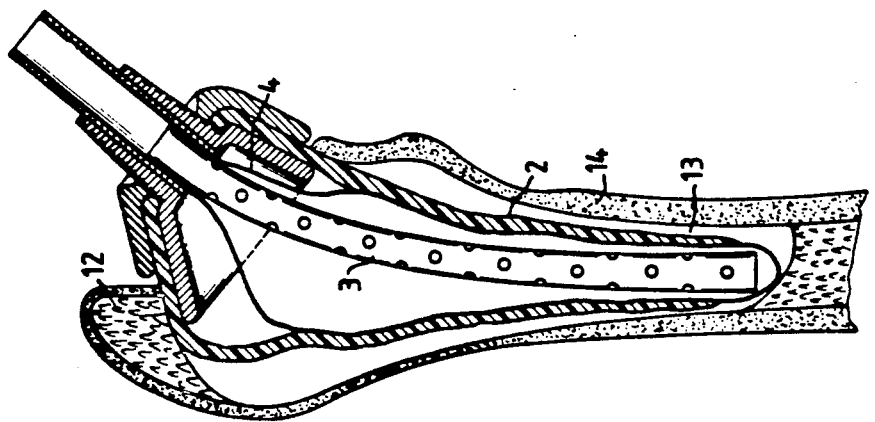

JOINT PROSTHESIS

BACKGROUND OF THE INVENTION

The invention relates to an endoprosthesis (joint prosthesis) frequently employed in orthopedic surgery. The prosthesis can be used for all types of endoprostheses, although the embodiment described hereinafter refers exclusively to a hip joint prosthesis.

The most varied indications may make it appear advisable to implant a substitute joint in a patient. Conventional endoprostheses, however, have only a service life of about five to eight years. The most frequent type of failure of such prostheses is their coming loose from the cement quiver or, for prostheses which have been inserted without cement, from the outer covering of the femur. The conventional endoprosthesis that has been inserted without cement has the drawback that the shaft extending into the bone (e.g. the femur) is insufficiently adapted to the shape of the marrow cavity intramedullary cavity due to the requirement for production in a certain number of sizes and the lack of a further curvature out of the single curvature plane (no distinction made between right and left). The resulting point contacts lead to locally very high transverse stresses and stress relief of the outer covering in the longitudinal directon and thus to resorptions in the upper region of the attachment of the prosthesis. The cemented endoprosthesis, although form-lockingly anchored in the cavity, constitutes, in its junction between prosthesis shaft and cement quiver, a component which is more resistant to bending by about one power of ten than the outer covering tube of the bone. The result is a reorientation of the flow of forces in the outer covering with large-area stress relief and local overstressing transverse to the orientation of the fibers.

SUMMARY OF THE INVENTION

Consequently, it is the object of the invention to provide a joint prosthesis which can be adapted individually in shape and rigidity distribution to the outer covering of the bone without significant compromises and which is able to absorb statically as well as dynamically the forces required for the general sequence of movement and to introduce them into the outer covering in a physiological manner so that there is less chance of loosening than with conventional prostheses.

This object and others to become apparent as the specification progresses, are accomplished by the invention, according to which, briefly stated, the joint prosthesis for insertion in a bone cavity comprises an adapter; a hollow, flexible prepreg member of hardenable material secured to the adapter; a hollow inflatable pressing member disposed in the prepreg member; and an arrangement for introducing fluid into the pressing member for inflating the same for causing the prepreg member to conform to the walls of the bone cavity.

It is noted that the term "prepreg" is the customary name given to fiber structures (glass, cabon, aramide or the like) which have already been wetted with a matrix plastic but have not yet hardened, i.e. whose polymerization process must still be initiated by extraneous influences such as heat, ultraviolet radiation, light, ultrasound or the like. The matrix plastic employed in this case is a plastic which, in its liquid form, is brought into contact with fibers or fabrics and, after hardening, produces a bond between the individual fibers. The structure contains these fibers in layers one on top of the other or in the form of oriented woven fabrics for the purpose of producing precisely defined, oriented rigidity as well as strength in the resulting laminate produced in conjunction with suitable matrix plastics.

Preferably, the prepreg member comprises specially cut strips which are fastened at their ends and take over the supporting and force introducing function of the prosthesis and which are hardened only during the surgery phase by the use of ultraviolet radiation or ultrasound and are thus adapted exactly to the outer cover of the bone. The force transmission to a joint head, for example an aluminum oxide ceramic sphere, is effected by means of a specially shaped adapter which is preferably made of a body compatible titanium alloy. By using a plastic, which is already known in dental medicine and which hardens under ultraviolet radiation, for embedding the fibers of the prepreg strips, there result no additional complications in connection with body compatibility of the entire implant. Rather, the same or better compatibility with the human body can be expected than for conventional prostheses. All auxiliary substances and devices required for the implantation may be produced of conventional sterilizable substances. The fiber material employed is glass, aramide or, if hardening is to be effected by ultrasound, also carbon.

The joint prosthesis according to the invention owes its longer service life, due to reduced danger of loosening and the danger of breakage connected therewith in the conventional prostheses, to the better individual adaptability of the supporting and force introducing structure of the implant (prepreg member), to the physiological conditions (shape, roughness) of the marrow cavity during insertion of the joint prosthesis in the course of surgery as well as to the fact that the introduction of force into the outer bone covering is better adapted to the physiological conditions (resistance to bending) with substantial avoidance of nonphysiological forces perpendicular to the fiber orientation of the outer bone covering. The novel joint prosthesis can be implanted without significantly greater effort than conventional prostheses and, in the case renewed surgery is required, it can be removed without undue effort. It can be used in all cases where the conventional prosthesis is presently being used and, in particular, if a physiological abnormality makes fitting a conventional prosthesis difficult or impossible because the latter is produced and available on the market only in certain sizes. Due to the high adaptability of the prosthesis according to the invention, its spectrum of application is significantly broader than that of the conventional type of prosthesis.

A preferred embodiment of the invention will be described with the aid of the drawings wherein the prepreg member and the pressing means are formed by separate members, while the insertion aid and the insertion member for the hardening agent are formed by a common member which performs both functions, which is hollow and permeable for a fluxing agent to swell the pressing agent as well as for radiation from a radiator provided to harden the prepreg member and guided in the hollow portion which simultaneously serves as insertion aid and insertion member.

BRIEF DESCRIPTION OF THE DRAWING

FIG. 1a is a longitudinal sectional view of a joint prosthesis according to a second preferred embodiment of the invention;

FIG. 2 is a longitudinal sectional view of the major components of the first preferred embodiment which has been inserted into an outer bone covering but has not yet been fastened therein;

FIG. 3 is a longitudinal sectional view of the arrangement according to FIG. 2 but during the hardening process; and FIG. 4 is a longitudinal sectional view of the entirely inserted and completed joint prosthesis according to the preferred embodiment.

DESCRIPTION OF THE FIRST PREFERRED EMBODIMENT

Figure 1:
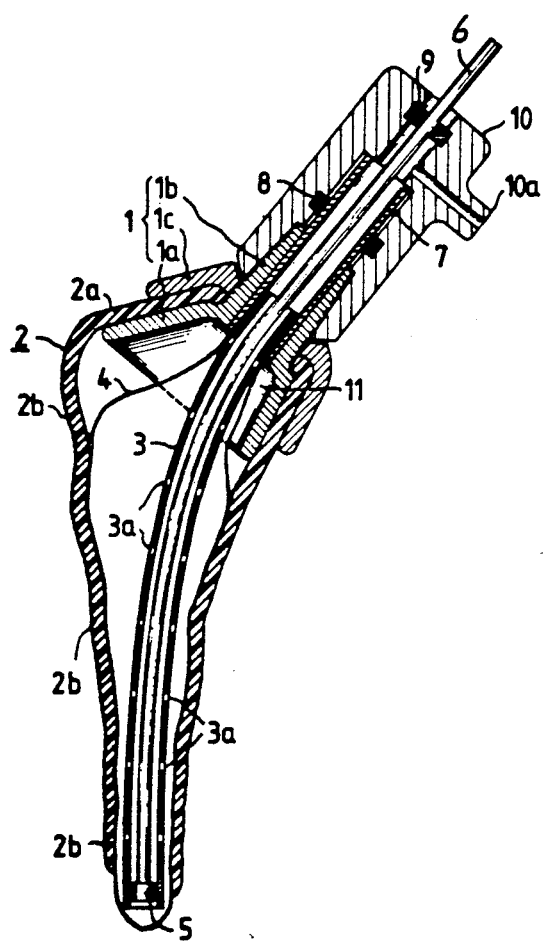
FIG. 1 is a longitudinal sectional view of a joint prosthesis according to a preferred embodiment of the invention.
Figure 1:
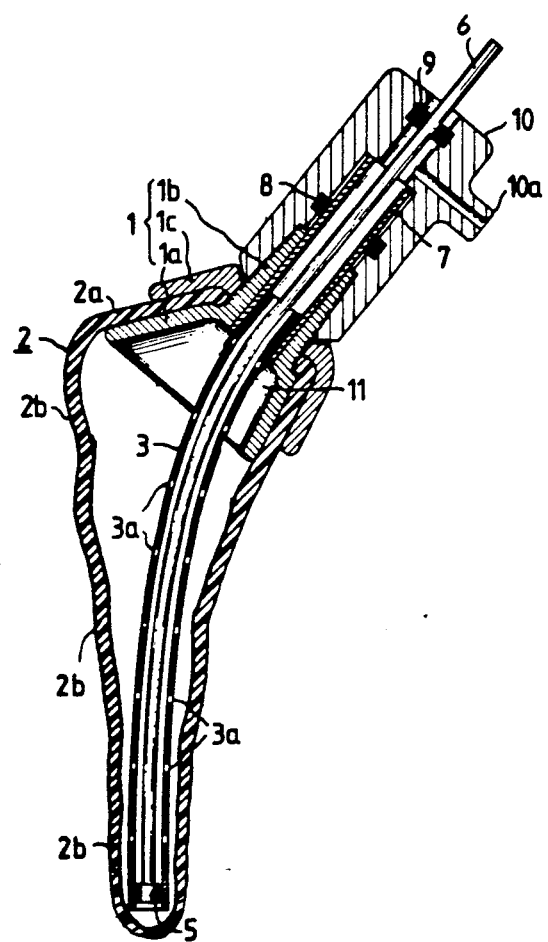

Turning now to FIG. 1, a two-part adaptor 1 which forms a clamping connection with a prepreg member 2 is provided with a holding member 1a, on whose threaded neck or nipple 1b there is screwed a sleeve member 1c. The upper region 2a of prepreg member 2 is clamped generally frustoconical and is in between members 1a and 1c. An insertion aid 3 brought through the threaded neck of adapter 1 and extending into the prepreg member simultaneously constitutes an insertion member. Pressing means 4 are provided in the interior of the prepreg member in the form of a foil bag and a swellable hose disposed at the lower end of insertion member 3 and sealed together therewith. A radiator 5 for ultraviolet or ultrasound radiation is insertable into the insertion member and is provided with transporting means 6. Moreover, there is provided a tube 7, seals 8 and 9 and an installation aid 10 including a coupling nipple 10a. The installation aid 10 comprises a screwable adapter equipped with the required connections for the passage of fluxing and hardening agents. Due to its larger accessible surface, the installation aid facilitates handling of the prosthesis during implantation.

An alternative embodiment is illustrated in FIG. 1a. This embodiment differs from the embodiment illustrated in FIG. 1 in that a separate pressing means, that is, the bag 4 is omitted and thus the prepreg member 2 itself constitutes the pressing means. For this purpose the prepreg member 2 is of a material substantially impermeable to the fluxing agent.

The prepreg member 2 comprises longitudinal strips and/or oppositely oriented spiral strips woven together in a suitable manner and clamped in between the holding member 1a and the screwed-on sleeve member 1c, thereby creating the impression of a feathered bell which, however—unless hardening does not occur until the surgery phase—is hardened in an upper region where it is fastened to adapter 1 while, in a lower region 2b it is still deformable and unhardened.

A tube 7 is inserted into the threaded neck 1and insertion aid 3 is inserted into the tube 7 in such a manner that a pressing agent 4 which is essentially impermeable to fluxing agents and, in particular, airtight and swellable, is clamped in at its upper end facing adapter 1. In order to swell this pressing agent 4, e.g. a foil or rubber bag, air can be blow into the bag through connection piece 10a, installation aid 10, tube 7, insertion aid 3 and through holes 3a provided in the bag 4. In order to prevent air from escaping at undesirable locations, seals 8 and 9 are provided. To assure that air does escape from cavity 11, ventilating means (not shown in detail) are provided in adapter 1 through which air can also be extracted (additionally or instead of the use of compressed air through connection piece 10a). The air pressed into pressing means 4 and/or extracted from cavity 11 is the fluxing means employed in the present embodiment with which pressing means 4 can be expanded so as to press the strips of prepreg member 2 against the interior wall of the bone in region 2b. To preserve this adapted state, the radiator 5 for hardening the prepreg member 2 is provided.

Insertion member 3 in the form of a tube of polyethylene or the like is provided for the insertion and simultaneously serves as insertion aid for the still flexible parts 2 (in region 2b) and 4.

The transporting means 6 for radiator 5 is an enlongate, resiliently yielding element which supplies energy to the radiator, either in the form of electrical energy or ultraviolet radiation, if transporting agent 6 is an optical conductor. Radiator 5 is transported at a defined withdrawal rate by means of drive means (not shown) which may be fastened to installation aid 10. The prepreg strips in region 2b may be designed in such a manner that empty spaces remain therebetween when they are pressed against the interior wall of a bone. Bone tissue will then later be able to grow into these interstices. The plastic material for the prepregs may be, for example, a material used in dentistry under the trade name "UVIOBOND".

FIG. 2 shows how the joint prosthesis of FIG. 1 is inserted into an outer bone covering after the spongiosa 12 have been substantially cleaned out of a marrow cavity 13.

FIG. 3 shows a later phase with pressed-on prepreg strip after air has been pressed into connection piece 10a with a slight excess pressure of approximately 0.8 bar. The ultraviolet or ultrasound radiator 5 has already passed halfway through marrow cavity 13 and its radiation, while penetrating members 3 and 4, has caused part of prepreg strip 2 to harden. No heat is generated during this process in contrast to the use of bone cement. Hardening takes approximately 6 to 8 minutes if ultraviolet light is used for the hardening process.

Turning now to FIG. 4, upon completion of the phase shown in FIG. 3, the no longer required auxiliary means, i.e. parts 3 through 10, are removed. A channel 15 is provided in adapter 1 for the removal of parts 3 through 7. This channel is enclosed by threaded neck 1b (FIG. 1) onto which installation aid 10 can be screwed to accomplish the processes of pressing on prepreg member 2 and hardening. After hardening, installation aid 10 is unscrewed and, after removal of the remaining auxiliary means, a joint bearing element, such as a joint head 16, e.g. an aluminum oxide ceramic ball is screwed on instead. For this purpose, threaded neck 1b is given a self-arresting, conical thread.

The further course of the surgical operation, including the insertion of the hip socket, takes place in a conventional manner.

While with the known hip joint prostheses the forces are introduced into the bone together with the generation of transverse forces, which, as a rule, the bone is unable to handle, in the joint prosthesis according to the invention the forces are introduced in the physiologically correct direction. On the one hand, the prosthesis exhibits a great moment of inertia and, on the other hand, the introduction forces are small per unit area, due to the large areas participating therein. Transverse stresses on the bone and a more or less point-shaped force transmission as it occurs in conventional prostheses are avoided, particularly since the structure itself is elastic and thus is able to follow the elastic deformations of the bone.

Repair of the prosthesis according to the invention is possible, contrary to the known prostheses, by replacing individual parts. Moreover, a new prosthesis can later be inserted without difficulty, due to the availability of a cavity, and such prosthesis may be of the conventional type or correspond to the embodiment according to the invention.

It will be understood that the above description of the present invention is susceptible to various modifications, changes and adaptations, and the same are intended to be comprehended within the meaning and range of equivalents of the appended claims.

What is claimed is:

1. A joint prosthesis kit comprising
   (a) a joint prosthesis for insertion in an intramedullary cavity; said joint prosthesis including
      (1) an adapter having a tubular nipple and securing means; said tubular nipple being capable of supporting a joint bearing element;
      (2) a hollow, flexible prepreg member of hardenable material attached to said adapter by said securing means; and
   (b) a hollow, inflatable fluid-impervious pressing means being receivable in said prepreg member and being removable therefrom; said prepreg member, after introduction into said intramedullary cavity, is, by inflating said fluid-impervious pressing means inside said prepreg member by introduction of a fluid thereinto through said nipple, expandable against the surface of the intramedullary cavity such that the prepreg member conforms to the surface of the intramedullary cavity where, upon hardening, said prepreg member forms a hard shell constituting a sole anchoring member of the prosthesis.

2. A joint prosthesis kit as defined in claim 1, wherein said nipple has a terminal nipple portion projecting outwardly from said prepreg member and constituting a support stud for a ball joint insertable thereon.

3. A joint prosthesis kit as defined in claim 1, further including means for introducing a fluid comprising a hose to be accommodated within said pressing means and having an end for connection to a fluid source.

4. A joint prosthesis kit as defined in claim 3, wherein said hose has a rigidity greater than that of said pressing means.

5. A joint prosthesis kit as defined in claim 1 wherein said prepreg member has a pre-hardened portion at least in a zone where it is secured to said adapter.

6. A joint prosthesis kit as defined in claim 1, wherein said pressing means comprises a foil bag.

7. A joint prosthesis kit as defined in claim 1, wherein said nipple being formed to support thereon a joint bearing element.

8. A joint prosthesis kit as defined in claim 1, further comprising an insertion means situated in said pressing means for removably receiving a hardening means for hardening the hardenable material of said prepreg member.

9. A joint prosthesis kit as defined in claim 8, wherein said insertion means comprises a tubular member connected to said nipple and adapted for introducing said fluid into said pressing means.

10. A joint prosthesis kit as defined in claim 1, further comprising a radiator means accommodated within said pressing means for irradiating said prepreg member to harden the hardenable material thereof.

11. A joint prosthesis kit as defined in claim 10, further comprising an insertion means for guiding said radiator means; said insertion means being situated in said pressing means.

12. A joint prosthesis kit as defined in claim 11, wherein said insertion means is a tubular member accommodating said radiator means; further comprising means for moving said radiator means within said tubular member.

13. A joint prosthesis kit as defined in claim 12 wherein an end of said tubular member is connected to said nipple.

14. A joint prosthesis kit as defined in claim 13, wherein the inner cross-sectional area of said tubular nipple is sufficiently large for removing therethrough said tubular member, said radiator means, said means for moving said radiator means and said pressing means.

15. A joint prosthesis kit as defined in claim 13, further comprising a mounting aid removably connectable with said nipple; said mounting aid including a port communicating with said tubular member through said tubular nipple.

16. A joint prosthesis for insertion in an intramedullary cavity comprising
   (a) an adapter capable of supportng a joint bearing element;
   (b) a hollow, flexible prepreg member of hardenable material clampingly connected to said adapter; and
   (c) means for introducing a fluid into the hollow prepreg member for expanding said prepreg member against the surface of the intramedullary cavity such that the prepreg member conforms to the surface of the intramedullary cavity where, upon hardening, said prepreg member forms a hard shell constituting a sole anchoring member of the prosthesis.

17. A joint prosthesis as defined in claim 16, wherein said prepreg member is fluid-impervious and further wherein said means for introducing the fluid is arranged for passing the fluid directly into the prepreg member for direct contact therewith.

18. A joint prosthesis inserted in an intramedullary cavity having an inner surface comprising
   (a) a hardened hollow prepreg member conforming closely to the inner surface of the intramedullary cavity and forming a shell constituting a sole anchoring member for the joint prosthesis; said shell having an opening surrounded by a marginal shell portion;
   (b) an adapter situated in a zone of said marginal shell portion and including
      (1) means for securing the adapter to the marginal shell portion;
      (2) a tubular, bilaterally open-ended nipple extending through said opening into said shell and having a terminal part projecting through said opening outwardly from said shell; said terminal part of said nipple being capable of supporting a joint bearing element.

19. A joint prosthesis as defined in claim 18, further comprising a joint bearing element secured to said terminal part of said nipple.

20. A joint prosthesis as defined in claim 18, wherein said prepreg member is generally frustoconical in a zone where it is secured to said adapter.

21. A joint prosthesis inserted in an intramedullary cavity having an inner surface, obtained by the process comprising the following steps:
(a) introducing a hollow, flexible prepreg member of hardenable material into the intramedullary cavity;
(b) inflating the prepreg member by a fluid introduced through a nipple affixed to said prepreg member for expanding said prepreg member to cause it to conform closely to said inner surface of said cavity; and
(c) hardening said prepreg member to transform the flexible prepreg member into a hard shell closely conforming to said inner surface; said shell constituting a sole anchoring member for the joint prosthesis.

22. A joint prosthesis as defined in claim 21, wherein the process further comprises the step of attaching, subsequent to step (b), a joint bearing element to a terminal part of the nipple projecting outwardly from said prepreg member.

* * * * *

UNITED STATES PATENT AND TRADEMARK OFFICE
CERTIFICATE OF CORRECTION

PATENT NO. : 4,562,598

DATED : January 7, 1986

INVENTOR(S) : Curt Kranz

It is certified that error appears in the above-identified patent and that said Letters Patent is hereby corrected as shown below:

In the heading of the patent please insert
-- [30] Foreign Application Priority Data
April 1st, 1981 [DE] Fed. Republic of Germany   P 31 13 531.5
October 23rd, 1981 [DE] Fed. Republic of Germany  P 31 42 730.8--.

Signed and Sealed this

Eighth Day of April 1986

[SEAL]

Attest:

DONALD J. QUIGG

Attesting Officer

Commissioner of Patents and Trademarks